United States Patent [19]

Jeanty

[11] 4,434,803

[45] Mar. 6, 1984

[54] DEVICE FOR FOETAL BLOOD SAMPLING IN UTERO

[75] Inventor: Philippe Jeanty, Ecaussinnes, Belgium

[73] Assignee: Laboratoires Biotrol S.A., Paris, France

[21] Appl. No.: 290,321

[22] Filed: Aug. 5, 1981

[30] Foreign Application Priority Data

Aug. 6, 1980 [FR] France .................................. 80 17416

[51] Int. Cl.³ .......................... A61B 6/00; A61B 10/00
[52] U.S. Cl. ..................................... 128/770; 128/763
[58] Field of Search ............... 128/347, 770, 753, 754, 128/760, 772, 658, 348

[56] References Cited

U.S. PATENT DOCUMENTS

| | | |
|---|---|---|
| 2,243,285 | 5/1941 | Pope . |
| 3,417,744 | 12/1968 | Mishkin et al. ........................ 128/658 |
| 3,508,545 | 4/1970 | Reif et al. ............................. 128/347 |
| 3,685,509 | 8/1972 | Bentall . |
| 3,810,456 | 5/1974 | Karman . |
| 3,967,625 | 7/1976 | Yoon . |
| 4,230,123 | 10/1980 | Hawkins, Jr. ........................ 128/658 |

*Primary Examiner*—George F. Lesmes
*Assistant Examiner*—Nancy A. B. Swisher
*Attorney, Agent, or Firm*—Oblon, Fisher, Spivak, McClelland & Maier

[57] ABSTRACT

A device for puncturing the umbilical cord of a foetus in utero. The device consists of two fixed tubes, a trocar, a stem with a resilient hook at one end, and a hollow needle. The trocar and the stem are adapted to slide in one of the tubes, and the hollow needle is adapted to slide in the other tube.

4 Claims, 4 Drawing Figures

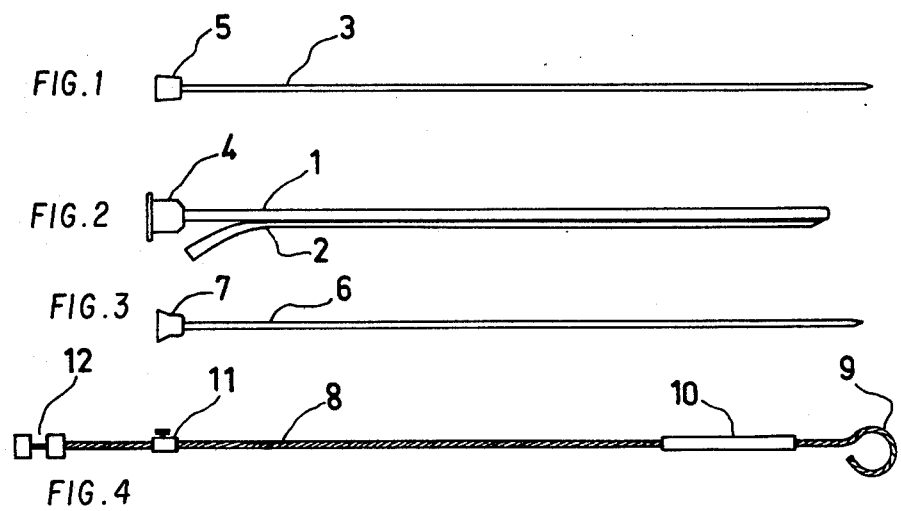

DEVICE FOR FOETAL BLOOD SAMPLING IN UTERO

FIELD OF THE INVENTION

This invention relates to a device for foetal blood sampling in utero. More particularly, it relates to a device arranged to reach the umbilical cord of a foetus in utero and take therefrom a certain amount of blood for the purpose of analysis. The analysis may be for the purpose of rapidly establishing a caryotype and/or effecting any other biological measurements or analyses.

BACKGROUND OF THE INVENTION

At present, there does not seem to exist any device allowing blood sampling from a foetus in utero. The sole samplings feasible atraumatically from such a foetus are of indirect character and are actually of the amniotic liquid rather than of the blood itself.

OBJECTS OF THE INVENTION

The principal object of the present invention is to provide a device which permits the caryotype of a foetus in utero to be rapidly established and/or which permits other biological measurements or analyses of the blood of a foetus in utero to be rapidly effected.

SUMMARY OF THE INVENTION

In accordance with the present invention, the above object and other objectives are attained by means of a device whereby the umbilical cord of a foetus in utero may be reached for taking therefrom a certain amount of blood.

The device of the invention basically comprises two parallel cannula-forming tubes, a trocar and a stem terminating in a resilient hook at one end thereof, and a hollow needle. The trocar and the stem are intended to slide within the one of the two tubes and are of greater length than the tube. The hollow needle is adapted to slide within the second of the two tubes and, it similarly is of greater length than the hollow tube in which it slides. Means are provided to position or removably interlock the trocar, the hook-bearing stem, and/or the hollow needle at the proximal end of the respective tube wherein they slide.

BRIEF DESCRIPTION OF THE DRAWINGS

FIG. 1 is a side view of the trocar which is a component of the presently preferred embodiment of the invention.

FIG. 2 is a side view of the two cannula-forming tubes which are components of the presently preferred embodiment of the invention.

FIG. 3 is a side view of the hollow needle which is a component of the presently preferred embodiment of the invention.

FIG. 4 is a side view of the stem which is a component of the presently preferred embodiment of the invention.

The various components are shown in disassembled condition for ease of illustration. The manner in which the components are assembled in use will become apparent from the description of the presently preferred embodiment which follows.

DETAILED DESCRIPTION OF THE PRESENTLY PREFERRED EMBODIMENT

The two tubes 1 and 2 may be cylindrical, as shown, or of other cross-sectional shapes, and they may be of identical or different diameters. In either case, they are fastened together (as by welding); along adjoining walls. Alternatively, they may be formed in a material having the required length and with a cross-sectional shape, preferably ovoid, adapted to accommodate jointly the two tube bores.

In the present state of development of the device, and taking into account the contemplated application, the maximum outer diameter of the two-tube assembly thus formed does not exceed about 3 mm. While this is also a non restrictive point, the length of these tubes is advantageously of about 15-17 cm, whereas the outer diameter of each of the tubes is of about 1 mm.

The distal end of the two-tube assembly (i.e., the end which is fed into the uterus) is preferably bevelled around its periphery so as to be as atraumatic as possible.

Trocar 3, which is intended to perforate the abdominal wall, is of conventional structure; its end is preferably cut as a threefold bevel. Preferably, the tube 1 wherein the trocar 3 is freely sliding carries a base 4, on the side which is proximal with respect to the user, and the trocar 3 has at its corresponding end a stopper 5 which engages the base 4 in use. To improve the removable attachment of the trocar 3 and in the tube 1 to impart to the trocar 3 a fixed position with respect to the tube system, it is advisable to provide the stopper 5 with a stud (not shown) and to form in the base 4 a longitudinal slot (not shown) adapted to lock the stud.

The hollow sampling or puncturing needle 6, which is to be inserted in the tube 2, should be free to slide in the latter. Its proximal is preferably provided with a base 7 which facilitates gripping the hollow needle 6 and which also acts as an abutment defining the end of the penetration stroke of the hollow needle 6 in the tube 2. The tube 2 may itself be provided with a base or other similar system adapted to facilitate the needle insertion and, if so required, to close up the tube 2. The hollow needle 6 should be of such length that, once it is inserted in the tube 2 down to its abutment, it extends from the other end to a sufficient distance to permit puncturing of a vessel in the umbilical cord.

According to the preferred embodiment, the proximal end of the tube 2 is bent apart from the first tube, this being mainly for the purpose of spacing the bore of the tube 2 from the base 4 and the stopper 5. In this case, it will be understood that the hollow needle 6 should be made of a flexible material, capable of following the curvature of the tube 2.

Stem 8 terminates at one end in a resilient hook 9. Stem 8 is intended to be inserted in the tube 1 once the system has been fed to the vicinity of the foetus and after removal of the trocar 3. Stem 8 is intended to catch the umbilical cord and bring it closely adjacent to the distal end of the tube 2. Once the umbilical cord has been brought into position by the hook 9, the hollow sampling needle 6 is inserted into the tube 2 and the umbilical cord wall is perforated, permitting the sampling of the blood flowing therein.

Therefore, the stem 8 should be adapted to be actuated and moved by the user so as to cause on the one hand, variation of the distance between its terminal hook 9 and the distal end of the tube system, and, on the other hand, variation of the hook curvature. This may be effected by any means known in the art, whereby the progress and favourable result of the operation may be checked.

A preferred stem 8 according to the invention comprises a hollow stem consisting of a winding with contiguous turns of a flexible cord, especially a metal wire, and of a core, also preferably of metal. After insertion of the core into the hollow stem, the core is unremovably secured to the distal end of the hollow stem. The distal portion of the stem 8 is treated to assume at rest a loop- or hook-like configuration which possesses sufficient resiliency to be capable of being stretched into a substantially rectilinear position and of resuming, upon stress removal, its hook-like configuration.

For the application referred to, this hook suitably has an inner diameter related to that of the involved umbilical cord. It should, however, be noted that the loop may have any shape and gape.

A member is preferably provided to make it easier for the user to straighten the hook into its rectilinear position and to insert the corresponding distal end into the first tube. Such a member may be, for example, a cylindrical sleeve 10 free to slide on stem 9 which carries the hook and adapted to be pushed back towards the proximal portion of the stem upon insertion thereof into the first tube. Moreover, the stem carrying the hook which holds the umbilical cord in the required position for its puncture may be temporarily blocked by a slide 11. The slide 11 is slidable over the stem end, but it is provided with a lateral setting screw whereby the stem may be held fast once the slide 11 has been brought to abut against the base 4 of the tube 1.

A suitable device 12, of the same type as those known in the art, provides relative motion of the aforesaid core with respect to the hollow stem and, thus, adjustment at will of the hook gape.

In practice, the actuation of the device according to the invention is subject to information collected by means of a suitable apparatus, which may be an echographic apparatus or an amnioscope.

To complete the device, the latter is connected, in use, to a blood collecting apparatus.

The multiple analyses and measurements made possible by the thus effected foetal blood takings may then be initiated.

What we claim is:

1. A device for sampling blood from the umbilical cord of a foetus in utero, said device comprising:
    (a) two cannula-forming tubes fixed to each other along their lengths, said cannula-forming tubes having outer dimensions suitable for passing through a mother's uterus to reach a foetus in the uterus and having proximal ends which, in use, are adjacent to the user and distal ends which, in use, are adjacent the umbilical cord;
    (b) a stem sized and shaped to fit slidably in one of said cannula-forming tubes, said stem having a distal end terminating in a resilient hook which is sized and shaped to catch the umbilical cord of a foetus in utero, said stem being sized and shaped so that, when it is inserted in said one of said cannula-forming tubes in use, the proximal end of said stem extends outwardly of the proximal end of said one of said cannula-forming tubes for manipulation by the user and the distal end of said stem extends outwardly of the distal end of said one of said cannula-forming tubes in position to hold the umbilical cord in position for sampling;
    (c) a hollow needle sized and shaped to fit slidably in the other of said cannula-forming tubes, said hollow needle having a sharp distal end and being sized and shaped so that, when it is inserted in said other of said cannula-forming tubes in use, the proximal end of said hollow needle extends outwardly of the proximal end of said other of said cannula-forming tubes for manipulation by the user and the distal end of said hollow needle extends outwardly from the distal end of said other of said cannula-forming tubes in position to puncture an umbilical cord being held by the resilient hook at the distal end of said stem;
    (d) a trocar sized and shaped to fit slidably in said one of said cannula-forming tubes, said trocar having a sharp distal end; and
    (e) means to secure said trocar in said one of said cannula-forming tubes with the distal end of said trocar extending forwardly of the distal end of said one of said cannula-forming tubes.

2. A device as recited in claim 1 wherein said cannula-forming tubes are cylindrical in cross section.

3. A device as recited in claim 1 wherein said stem comprises:
    (a) a hollow outer sheath composed of contiguous windings of a flexible cord and
    (b) a core disposed inside said hollow outer sheath, the distal end of said core being formed into the resilient hook at the distal end of said stem.

4. A device as recited in claim 3 wherein:
    (a) said core is slidably fitted within said hollow outer sheath and
    (b) the resilient hook at the distal end of said core is straightened out when disposed within said hollow outer sheath but returns to its hook shape when moved forward of the distal end of said hollow outer sheath.

* * * * *